US012023417B2

United States Patent
Maimon et al.

(10) Patent No.: US 12,023,417 B2
(45) Date of Patent: Jul. 2, 2024

(54) METHOD FOR PRE-STRETCHING IMPLANTABLE BIOCOMPATIBLE MATERIALS, AND MATERIALS, AND DEVICES PRODUCED THEREBY

(71) Applicant: Edwards Lifesciences Corporation, Irvine, CA (US)

(72) Inventors: David Maimon, Atlit (IL); Tamir S. Levi, Zikhron Yaakov (IL); Elena Sherman, Pardes Hana (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1017 days.

(21) Appl. No.: 16/933,866

(22) Filed: Jul. 20, 2020

(65) Prior Publication Data

US 2020/0345894 A1 Nov. 5, 2020

Related U.S. Application Data

(63) Continuation of application No. PCT/US2019/014591, filed on Jan. 22, 2019.
(Continued)

(51) Int. Cl.
*A61L 27/36* (2006.01)
*A61F 2/24* (2006.01)
(Continued)

(52) U.S. Cl.
CPC ........ *A61L 27/3691* (2013.01); *A61F 2/2415* (2013.01); *A61L 27/3625* (2013.01);
(Continued)

(58) Field of Classification Search
CPC ............................ A61L 27/3691; B29C 55/02
See application file for complete search history.

(56) References Cited

U.S. PATENT DOCUMENTS 2,393,580 A 1/1946 Weiskopf
4,120,649 A 10/1978 Schechter
(Continued)

FOREIGN PATENT DOCUMENTS

EP 0169259 A1 1/1986
EP 2394673 A1 12/2011
(Continued)

OTHER PUBLICATIONS

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.
(Continued)

*Primary Examiner* — Jacob T Minskey
*Assistant Examiner* — Wayne K. Swier
(74) *Attorney, Agent, or Firm* — KLARQUIST SPARKMAN, LLP (57) ABSTRACT

A method is provided for pre-stretching implantable biocompatible materials, such as material to be incorporated into an implantable device. A sheet of implantable biocompatible material is attached to one or more tensioning members, where tension is applied along one or more axes. Tension is applied for a period of time, and at an appropriate force, to produce a desired degree of thinning or pre-stretching of the implantable biocompatible material. During the tensioning, the implantable biocompatible material is maintained at an elevated temperature, such as a temperature that is at least substantially a temperature of an environment into which the material will be implanted.

17 Claims, 4 Drawing Sheets

Related U.S. Application Data (60) Provisional application No. 62/620,614, filed on Jan. 23, 2018.

(51) Int. Cl.
*B29C 55/02* (2006.01)
*B29L 31/00* (2006.01)

(52) U.S. Cl.
CPC .......... *A61L 27/3641* (2013.01); *B29C 55/02* (2013.01); *A61F 2240/001* (2013.01); *A61L 2430/20* (2013.01); *A61L 2430/40* (2013.01); *B29K 2995/0056* (2013.01); *B29L 2031/7534* (2013.01)

(56) References Cited

U.S. PATENT DOCUMENTS

| | | |
|---|---|---|
| 4,323,358 A | 4/1982 | Lentz et al. |
| 4,350,492 A | 9/1982 | Wright et al. |
| 4,372,743 A | 2/1983 | Lane |
| 4,378,224 A | 3/1983 | Nimni et al. |
| 4,402,697 A | 9/1983 | Pollock et al. |
| 4,405,327 A | 9/1983 | Pollock |
| 4,481,009 A | 11/1984 | Nashef |
| 4,553,974 A | 11/1985 | Dewanjee |
| 4,624,822 A | 11/1986 | Arru et al. |
| 4,647,283 A | 3/1987 | Carpentier et al. |
| 4,648,881 A | 3/1987 | Carpentier et al. |
| 4,758,151 A | 7/1988 | Arru et al. |
| 4,770,665 A | 9/1988 | Nashef |
| 4,776,853 A | 10/1988 | Klement et al. |
| 4,786,287 A | 11/1988 | Nashef et al. |
| 4,838,888 A | 6/1989 | Nashef |
| 4,865,871 A | 9/1989 | Livesey et al. |
| 4,885,005 A | 12/1989 | Nashef et al. |
| 4,958,008 A | 9/1990 | Petite et al. |
| 4,976,733 A | 12/1990 | Girardot |
| 5,002,566 A | 3/1991 | Carpentier et al. |
| 5,051,401 A | 9/1991 | Sikes |
| 5,080,670 A | 1/1992 | Imamura et al. |
| 5,094,661 A | 3/1992 | Levy et al. |
| 5,104,405 A | 4/1992 | Nimni |
| 5,116,564 A | 5/1992 | Jansen et al. |
| 5,147,514 A | 9/1992 | Mechanic |
| 5,154,007 A | 10/1992 | Piunno et al. |
| 5,200,399 A | 4/1993 | Wettlaufer et al. |
| 5,215,541 A | 6/1993 | Nashef et al. |
| 5,279,612 A | 1/1994 | Eberhardt |
| 5,329,846 A | 7/1994 | Bonutti |
| 5,397,353 A | 3/1995 | Oliver et al. |
| 5,437,287 A | 8/1995 | Phillips et al. |
| 5,447,536 A | 9/1995 | Girardot et al. |
| 5,460,962 A | 10/1995 | Kemp |
| 5,476,516 A | 12/1995 | Seifter et al. |
| 5,509,932 A | 4/1996 | Keogh et al. |
| 5,558,875 A | 9/1996 | Wang |
| 5,595,571 A | 1/1997 | Jaffe et al. |
| 5,613,982 A | 3/1997 | Goldstein |
| 5,645,587 A | 7/1997 | Chanda et al. |
| 5,674,298 A | 10/1997 | Levy et al. |
| 5,697,972 A | 12/1997 | Kim et al. |
| 5,713,953 A | 2/1998 | Vallana et al. |
| 5,720,777 A | 2/1998 | Jaffe et al. |
| 5,720,894 A | 2/1998 | Neev et al. |
| 5,733,339 A | 3/1998 | Girardot et al. |
| 5,746,775 A | 5/1998 | Levy et al. |
| 5,766,520 A | 6/1998 | Bronshtein |
| 5,769,780 A | 6/1998 | Hata et al. |
| 5,782,914 A | 7/1998 | Schankereli |
| 5,782,931 A | 7/1998 | Yang et al. |
| 5,843,180 A | 12/1998 | Jaffe et al. |
| 5,843,181 A | 12/1998 | Jaffe et al. |
| 5,855,620 A | 1/1999 | Bishopric et al. |
| 5,862,806 A | 1/1999 | Cheung |
| 5,873,812 A | 2/1999 | Ciana et al. |
| 5,899,936 A | 5/1999 | Goldstein |
| 5,911,951 A | 6/1999 | Girardot et al. |
| 5,919,472 A | 7/1999 | Trescony et al. |
| 5,921,980 A | 7/1999 | Kirn |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,993,844 A | 11/1999 | Abraham et al. |
| 6,008,292 A | 12/1999 | Lee et al. |
| 6,017,741 A | 1/2000 | Keogh |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |
| 6,166,184 A | 12/2000 | Hendriks et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,293,970 B1 | 9/2001 | Wolfinbarger, Jr. et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,375,680 B1 | 4/2002 | Carlyle |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,482,199 B1 | 11/2002 | Neev |
| 6,506,339 B1 | 1/2003 | Girardot et al. |
| 6,509,145 B1 | 1/2003 | Torrianni |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,589,591 B1 | 7/2003 | Mansouri et al. |
| 6,605,667 B1 | 8/2003 | Badejo et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,682,559 B2 | 1/2004 | Myers et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |
| 6,797,000 B2 | 9/2004 | Simpson et al. |
| 6,872,226 B2 | 3/2005 | Cali et al. |
| 6,878,168 B2 | 4/2005 | Carpentier et al. |
| 6,908,591 B2 | 6/2005 | MacPhee et al. |
| 6,911,043 B2 | 6/2005 | Myers et al. |

(56) References Cited

U.S. PATENT DOCUMENTS

| | | | |
|---|---|---|---|
| 6,919,172 B2 | 7/2005 | DePablo et al. |
| 7,008,763 B2 | 3/2006 | Cheung |
| 7,029,434 B2 | 4/2006 | Carpentier et al. |
| 7,037,333 B2 | 5/2006 | Myers et al. |
| 7,063,726 B2 | 6/2006 | Crouch et al. |
| 7,078,163 B2 | 7/2006 | Torrianni |
| 7,141,064 B2 | 11/2006 | Scott et al. |
| 7,143,769 B2 | 12/2006 | Stoltz et al. |
| 7,214,344 B2 | 5/2007 | Carpentier et al. |
| 7,238,200 B2 | 7/2007 | Lee et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,367,969 B2 | 5/2008 | Stoltz et al. |
| RE40,570 E | 11/2008 | Carpentier et al. |
| 7,498,565 B2 | 3/2009 | Silberberg et al. |
| 7,579,381 B2 | 8/2009 | Dove |
| 7,594,974 B2 | 9/2009 | Cali et al. |
| 7,648,676 B2 | 1/2010 | Mills et al. |
| 7,682,304 B2 | 3/2010 | Heyninck-Jantz et al. |
| 7,914,569 B2 | 3/2011 | Nguyen et al. |
| 7,919,112 B2 | 4/2011 | Pathak et al. |
| 7,972,376 B1 | 7/2011 | Dove et al. |
| 8,007,992 B2 | 8/2011 | Tian et al. |
| 8,038,708 B2 | 10/2011 | Case et al. |
| 8,043,450 B2 | 10/2011 | Cali et al. |
| 8,075,615 B2 | 12/2011 | Eberhardt et al. |
| 8,105,375 B2 | 1/2012 | Navia et al. |
| 8,136,218 B2 | 3/2012 | Millwee et al. |
| 8,308,797 B2 | 11/2012 | Paniagua et al. |
| 8,361,144 B2 | 1/2013 | Fish et al. |
| 8,377,143 B2 | 2/2013 | Hamby et al. |
| 8,475,827 B2 | 7/2013 | Hamby et al. |
| 2001/0000804 A1 | 5/2001 | Goldstein et al. |
| 2001/0025196 A1 | 9/2001 | Chinn et al. |
| 2001/0027344 A1 | 10/2001 | Bonutti |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0091441 A1 | 7/2002 | Guzik |
| 2002/0111532 A1 | 8/2002 | Pathak et al. |
| 2003/0035843 A1* | 2/2003 | Livesey | A61K 39/12 |
| | | | 424/549 |
| 2003/0125805 A1 | 7/2003 | Johnson et al. |
| 2003/0135284 A1 | 7/2003 | Crouch et al. |
| 2003/0167089 A1 | 9/2003 | Lane |
| 2003/0212454 A1 | 11/2003 | Scott et al. |
| 2004/0030381 A1 | 2/2004 | Shu |
| 2004/0086543 A1 | 5/2004 | Keogh et al. |
| 2004/0158320 A1 | 8/2004 | Simionescu et al. |
| 2005/0010773 A1 | 1/2005 | Lapstun et al. |
| 2005/0119736 A1 | 6/2005 | Zilla et al. |
| 2005/0136510 A1 | 6/2005 | Hendriks et al. |
| 2005/0211680 A1 | 9/2005 | Li et al. |
| 2006/0084957 A1 | 4/2006 | Delfyett et al. |
| 2006/0099326 A1 | 5/2006 | Keogh et al. |
| 2006/0110370 A1 | 5/2006 | Pathak et al. |
| 2006/0159641 A1 | 7/2006 | Girardot et al. |
| 2006/0193885 A1 | 8/2006 | Leonard Neethling et al. |
| 2006/0210960 A1 | 9/2006 | Livesey et al. |
| 2006/0217804 A1 | 9/2006 | Dove |
| 2006/0217805 A1 | 9/2006 | Dove |
| 2007/0050014 A1 | 3/2007 | Johnson |
| 2007/0073392 A1 | 3/2007 | Heyninck-Jantz et al. |
| 2007/0203576 A1 | 8/2007 | Lee et al. |
| 2007/0254005 A1 | 11/2007 | Pathak et al. |
| 2008/0243248 A1* | 10/2008 | Stone | A61L 27/50 |
| | | | 623/13.12 |
| 2008/0302372 A1 | 12/2008 | Davidson et al. |
| 2008/0319166 A1 | 12/2008 | Shen |
| 2009/0041729 A1 | 2/2009 | Wolfinbarger, Jr. et al. |
| 2009/0130162 A2 | 5/2009 | Pathak et al. |
| 2009/0137999 A1 | 5/2009 | Silberberg et al. |
| 2009/0188900 A1 | 7/2009 | Cali et al. |
| 2009/0326524 A1 | 12/2009 | Cali et al. |
| 2010/0036484 A1 | 2/2010 | Hariton et al. |
| 2011/0092966 A1 | 4/2011 | Guo et al. |
| 2011/0177150 A1 | 7/2011 | Pathak et al. |
| 2011/0214398 A1 | 9/2011 | Liburd et al. |
| 2011/0238167 A1 | 9/2011 | Dove et al. |
| 2011/0295363 A1 | 12/2011 | Girard et al. |
| 2011/0300625 A1 | 12/2011 | Paniagua et al. |
| 2011/0306124 A1 | 12/2011 | Strasly et al. |
| 2011/0311493 A1 | 12/2011 | Dove et al. |
| 2012/0035720 A1 | 2/2012 | Cali et al. |
| 2012/0059487 A1 | 3/2012 | Cunanan et al. |
| 2012/0067855 A1 | 3/2012 | Guo et al. |
| 2012/0078356 A1 | 3/2012 | Fish et al. |
| 2012/0095551 A1 | 4/2012 | Navia et al. |
| 2012/0123557 A1 | 5/2012 | Carpentier et al. |
| 2012/0185038 A1 | 7/2012 | Fish et al. |
| 2012/0328905 A1 | 12/2012 | Guo et al. |
| 2013/0122583 A1 | 5/2013 | Neethling |
| 2013/0238088 A1 | 9/2013 | Navia et al. |
| 2015/0088247 A1 | 3/2015 | L'Heureux et al. |
| 2016/0022254 A1 | 1/2016 | McCarthy |

FOREIGN PATENT DOCUMENTS

| | | | | |
|---|---|---|---|---|
| WO | 8401894 A1 | 5/1984 | | |
| WO | 9511047 A1 | 4/1995 | | |
| WO | 9522361 A1 | 8/1995 | | |
| WO | 9534332 A1 | 12/1995 | | |
| WO | 9613227 A1 | 5/1996 | | |
| WO | 9807452 A1 | 2/1998 | | |
| WO | 9843556 A1 | 10/1998 | | |
| WO | 0032252 A1 | 6/2000 | | |
| WO | 2004082536 A1 | 9/2004 | | |
| WO | 2006026325 A2 | 3/2006 | | |
| WO | 2006099334 A2 | 9/2006 | | |
| WO | WO-2011008150 A1 * | 1/2011 | ............... | A61F 2/08 |
| WO | 2013009851 A2 | 1/2013 | | |
| WO | WO-2017062199 A1 * | 4/2017 | ........... | A61F 2/2415 |

OTHER PUBLICATIONS

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified and Cross-Linked Bovine Pericardium as a Ligament Substitute," Journal of Biomedical Materials Research, vol. 21, No. 12, pp. 1383-1394, 1987, University of Arizona Health Science Center, Tucson, AZ.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./Feb. 2011.

Grabenwoger, M. et al. "Decreased Tissue Reaction to Bioprosthetic Heart Valve Material after L-glutaimc acid Treatment. A Morphological Study." J. Biomed Mater. Res. Sep. 1992;26(9):1231-40.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Hauschka, P., et al., "Direct Identification of the Calcium-Binding Amino Acid, γ-Carboxyglutamate, in Mineralized Tissue," Proc. Nat. Acad. Sci, vol. 72, No. 10, pp. 3925-3929, Oct. 1975.

Jayakrishnan, A., et al., "Glutaraldehyde as a Fixative in Bioprostheses and Drug Delivery Matrices," Biomaterials, vol. 17, Issue 5, 1996, pp. 471-484.

Khora, Eugene, "Methods for the Treatment of Collagenous Tissues for Bioprostheses," Biomaterials, vol. 18, Issue 2, Jan. 1997, pp. 95-105.

Liao, K., et al., "Mechanical Stress: An Independent Determinant of Early Bioprosthetic Calcification in Humans," Ann. Throac. Surg 2008;86:491-495.

(56) References Cited

OTHER PUBLICATIONS

Neethling, W., et al., "Enhanced Biostability and Biocompatibility of Decellularized Bovine Pericardium, Crosslinked with an Ultra-Low Concentration Monomeric Aldehyde and Treated with Adapt®," J. Heart Valve Dis. 2008; 17:456-464.

Olde Damink, L.H.H., et al., "Influence of Ethylene Oxide Gas Treatment on the in vitro Degradation Behavior of dermal Sheep Collagen," Journal of Biomedical Materials Resarch, vol. 29, pp. 149-155, 1995.

R Parker, et al. Storage of Heart Valve Allografts in Glycerol With Subsequent Antibiotic Sterilisation, Thorax, 1978, 638-645, vol. 33:5, British Thoracic Society, London, UK.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterials, vol. 21, pp. 2215-2231, 2000.

Trantina-Yates AE, et al. "Detoxification of Top Enhanced, Diamine-Extended Glutaraldehyde Fixation Significantly Reduces Bioprosthetic Root Calcification in the Sheep Model," J. Heart Valve Dis. Jan. 2003; 12 (1):93-100.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

\* cited by examiner

METHOD FOR PRE-STRETCHING IMPLANTABLE BIOCOMPATIBLE MATERIALS, AND MATERIALS, AND DEVICES PRODUCED THEREBY

CROSS REFERENCE TO RELATED APPLICATIONS

This application is a continuation of International Application No. PCT/US2019/014591, filed Jan. 22, 2019, which claims the benefit of U.S. Application No. 62/620,614, filed Jan. 23, 2018, the entire disclosures which are incorporated by reference for all purposes.

FIELD

The present disclosure concerns methods for pre-stretching implantable biocompatible materials and materials produced thereby, as well as implantable devices incorporating such materials. Particular embodiments relate to pre-stretching implantable biocompatible materials maintained at a temperature that is at least about a temperature of an environment into which a device incorporating such material will be implanted.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

A particular type of artificial valve is constructed from natural tissue or a synthetic material coupled, such as by sewing, to a frame. Prosthetic heart valves that are implanted surgically in an open-chest procedure typically have a rigid frame that is sutured to the native valve annulus. Transcatheter heart valves have radially collapsible and expandable frames to permit delivery of the prosthetic valve through the patient's vasculature using a delivery catheter without the need to open the patient's chest.

The material that is attached to a valve frame, particularly material that forms prosthetic valve leaflets, can be subject to various mechanical stresses during the life of the valve, including during construction of the valve, preparation of the valve for implantation, implantation, and after implantation. For instance, during construction, the material may be stretched to fit over a frame or individual frame elements. The valve may be crimped to a reduced diameter for storage and implantation, and then expanded during implantation (e.g., after delivery to an implantation site). After implantation, during operation of the valve in a subject, the material, particularly material in the valve leaflets, may experience repetitive stresses from opening and closing of the valve.

The stresses experienced by material used in prosthetic valves can negatively affect the construction and performance of such prosthetic valves. For instance, materials used in the construction of prosthetic valves typically exhibit viscoelastic properties. In particular, the materials may be prone to stretch, or creep, over time. As the materials stretch, they may lose contact with frame elements (e.g., sag) or may rub against or otherwise contact frame elements, which can potentially prematurely wear the material or cause the material to become damaged. In addition, if the size of the material changes due to stretching, or the material experiences a change in its mechanical properties, the valve may no longer function as intended, such as having leaflets that no longer properly coapt, which can cause regurgitation through the valve.

The properties of the material used in prosthetic valves can affect the construction or performance of the valve in other ways. For example, the degree to which a valve can be crimped, and its performance during crimping (such as achieving a desired configuration, such as folding of the material relative to frame components) can be affected by the thickness of the material. In at least some cases, thinner materials can provide smaller crimp profiles and more consistent folding of the material.

At least some prior methods of obtaining thinner materials, such as removing surface material or compression, can alter the properties of the material. In the case of tissue, such as pericardial tissue, removing surface material can affect other properties of the material (such as elasticity or rigidity), as different layers of the material can include different components, such as different amounts or orientations of collagen and elastin. In the case of compression, compressing material to reduce its thickness can change the available compression ratio. That is, if the material is pre-compressed, it may be less able to undergo further compression during later assembly or use of a prosthetic valve that incorporates the material.

SUMMARY

Certain embodiments of the present disclosure relate to methods for pre-stretching an implantable biocompatible material, such as pericardial tissue. The pre-stretched implantable biocompatible material can be incorporated into implantable devices, including a heart valve prosthesis.

In one representative embodiment, a disclosed method includes applying a tensioning force of between about 300 grams and about 4000 grams to a sheet of implantable biocompatible material, such as bovine or porcine pericardial tissue. While the sheet of implantable biocompatible material is under tension, the temperature of the sheet is maintained at a temperature that is at least substantially as high as a temperature of an environment into which at least a portion of the implantable biocompatible material will be implanted, such as a physiological environment. For example, the temperature can be between about 30° C. and about 46° C. In some cases, the implantable biocompatible material can be maintained at a temperature that is between about the temperature of an environment into which at least a portion of the implantable biocompatible material will be implanted and a temperature less than a temperature beyond which the implantable biocompatible material will experience damage from the temperature during the course of the stretching. Maintaining the temperature of the implantable biocompatible material at a temperature higher than that of an implantation environment, such as a temperature close to a temperature at which the implantable biocompatible material may become damaged by the temperature, can reduce the time needed to obtain a desired degree of pre-stretching, as well as reducing the tension to be applied to achieve the desired degree of pre-stretching.

The sheet can be maintained under tension until the sheet experiences a substantial decrease in an elongation rate of the sheet. The time the sheet is maintained under tension can be between about 11 days and about 45 days, or until the elongation rate is less than about 25% of an average initial elongation rate, where the average initial elongation rate is the average elongation rate of the first hour of applying tension to the sheet.

The foregoing and other objects, features, and advantages of the disclosure will become more apparent from the following detailed description, which proceeds with reference to the accompanying figures.

DETAILED DESCRIPTION

Figure 1:
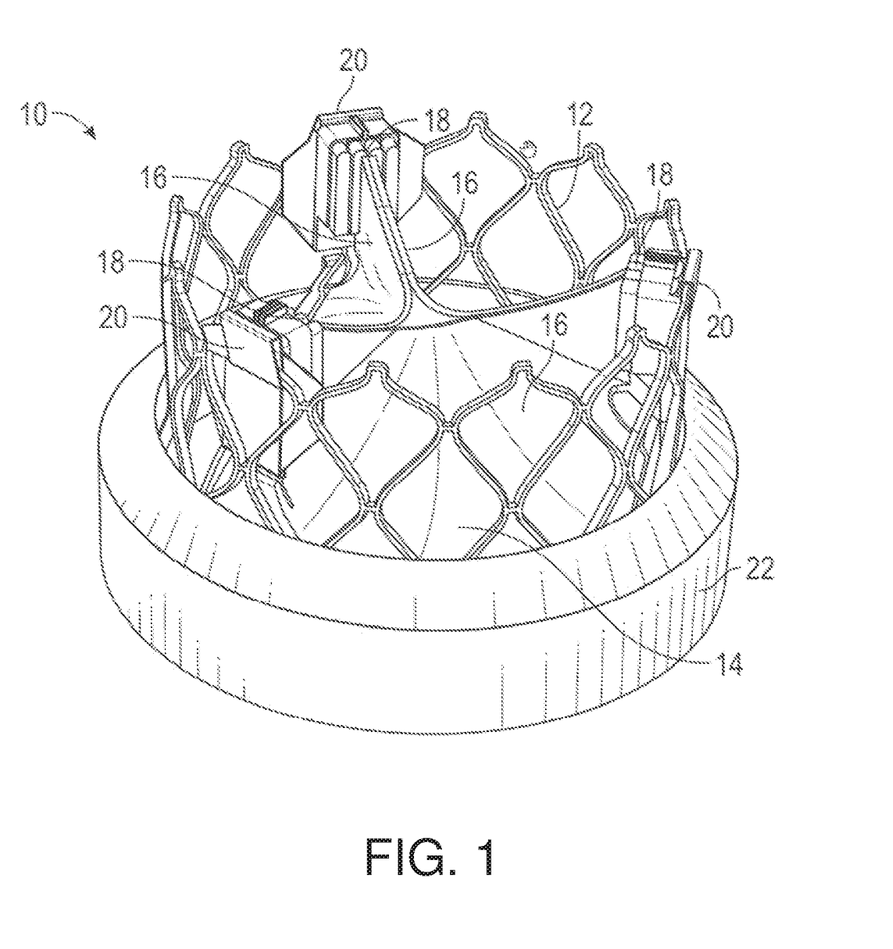
FIG. 1 is a perspective view of a representative embodiment of a prosthetic heart valve.

The present disclosure provides methods for pre-stretching implantable biocompatible materials with viscoelastic characteristics, such as material to be incorporated into an implantable device, as well as materials produced by such methods and implantable devices incorporating such materials. FIG. 1 shows an exemplary implantable device with which pre-stretched implantable materials of the present disclosure can be used, in the form of a prosthetic heart valve 10.

The prosthetic heart valve 10 comprises a stent or frame 12 and a valvular structure 14 supported by the frame and configured to regulate the flow of blood through the prosthetic valve. In some embodiments, the prosthetic valve 10 is adapted to be implanted in the native aortic valve and can be implanted in the body using, for example, a delivery apparatus as known in the art. The frame 12 can comprise a plastically expandable material, such as stainless steel, a nickel based alloy (e.g., a nickel-cobalt-chromium alloy), polymers, or combinations thereof, so that the frame 12 plastically expands when the prosthetic valve expands from a crimped, radially compressed configuration to the radially expanded configuration shown in FIG. 1 upon inflation of an expansion mechanism, such as a balloon of a balloon catheter, one or more mechanical actuators, or another type of expansion means. In alternative embodiments, the frame 12 can comprise a self-expandable material, such as Nitinol, so that the frame can self-expand from a radially compressed configuration to a radially expanded configuration when released from a delivery sheath or other restraining device.

The valvular structure 14 can comprise a plurality of leaflets 16 mounted inside of the frame 12. The opposing sides of each leaflet 16 can be paired with adjacent leaflets to form commissures 18 of the valvular structure. The commissures 18 can be mounted to the frame 12 via reinforcing members 20. The prosthetic valve 10 can also include a sealing member 22 mounted on the outside of the frame 12. The sealing member 22 is configured to help seal the prosthetic valve 10 against surrounding tissue and prevent or minimize perivalvular leakage. The leaflets 16 can be made from any of various suitable implantable biocompatible materials, including natural tissue, such as bovine pericardial tissue (or pericardial tissue from other sources) or synthetic materials, such as any of various fabrics or non-fabric materials (e.g., polyurethane). The leaflets 16 can be produced using any of the methods and/or techniques disclosed herein.

The reinforcing members 20 and the sealing member 22 desirably are made of a fabric material, such as polyethylene terephthalate (PET) fabric, although non-fabric materials and natural tissue also could be used. Further details of the prosthetic valve 10, including methods for assembling the leaflets 16 and the sealing member 22 on the frame 12, are disclosed in U.S. Patent Application Publication No. 2018/0028310. Other types of prosthetic heart valves that can incorporate leaflets formed using implantable biocompatible materials produced via the methods disclosed herein are described in U.S. Pat. Nos. 7,510,575; 7,993,394; and 9,393,110.

According to a disclosed technique for producing a pre-stretched implantable biocompatible material, a sheet of implantable biocompatible material is attached to one or more tensioning members, where tension is applied along one or more axes. Tension is applied for a period of time, and at an appropriate force, to produce a desired degree of thinning or pre-stretching of the implantable biocompatible material. During the tensioning, the implantable biocompatible material can be maintained at an elevated temperature, such as a temperature that is at least substantially a temperature of an environment into which the material will be implanted.

In particular aspects, the implantable biocompatible material can be maintained at a temperature that is higher than the environment into which the material will be implanted, but less than a temperature where the material would experience temperature-related damage. The elevated temperature can be selected such that pre-stretching occurs to a desired degree over a particular time period and using a particular degree of tension. For instance, at least approximately equivalent pre-stretching can be achieved using shorter times and greater tension and/or higher temperature, or using longer times and lower tension and/or lower temperatures.

Pre-stretched implantable biocompatible materials according to the present disclosure can provide a variety of benefits. For example, when stretching is carried out such that additional elongation under the applied conditions has essentially ceased, if the stretching conditions are similar to the implantation environment, a device incorporating the stretched implantable material is likely to be more stable after implantation. More particularly, if the implantable biocompatible material is incorporated into a prosthetic valve, the valve may be more durable, and the chances of the valve leaflets contacting components of a valve frame may be reduced (which can, among other things, reduce the chances of the leaflets being thereby damaged).

In some cases, valves can be manipulated between a compressed, or crimped, state (such when the valve is being stored or during delivery of the valve to an implantation site in a subject) and an expanded, or uncrimped, state (such as when the valve has been delivered to an implantation site and fully deployed). Pre-stretching material used in the valve can help ensure that the valve materials do not significantly stretch or elongate after the valve is implanted and expanded, which can improve long term valve stability.

As stretching does not typically affect the density and, at least some cases, the internal structure, of the implantable biocompatible material, at least certain physical and mechanical properties of the stretched material may be the same or more similar to the native (unstretched) material that materials produce using other thinning techniques. In particular, when thinning is carried out by removing material from the surface of an implantable biocompatible material, the material produced thereby may still undergo additional thinning if the material is subjected to tension, such as during or after incorporation of the material into an implantable device or implantation of such a device.

The disclosed methods can be used with any suitable implantable biocompatible material. Implantable biocompatible materials can be of biological origin or can be synthetic. Biological materials can include tissues of human origin or animal tissue. Sources of animal tissue can include bovine, equine, or porcine sources. Biological tissue, whether of human or animal origin, can be taken from tissues such as blood vessels, cardiac valves, dura mater, ligaments, pericardium, small intestinal submucosa ("SIS tissue"), and tendons. Synthetic materials can include polytetrafluoroethylene, poly-di-methyl-siloxane, poly-glycolic acid, poly-4-hydroxybutyrate, polyhydroxyalkanoate, and polyethylene terephthalate (PET, e.g., Dacron® PET). In general, techniques according to the present disclosure can be used with any viscoelastic material which is to be used in an implantable device.

Biological materials can be preprocessed before stretching. Preprocessing can include, for example, cleaning, defatting, and the like. Such materials are often cut or resected into pieces or sheets. For example, bovine pericardial sacs can be cut into rectangular pieces with a long dimension of about 30-40 cm, which can then be subjected to the stretching procedure disclosed herein. Smaller pieces of tissue can also be selected from these larger sheets based on particular criteria, for example, thickness, fiber direction, consistency, and/or convenience of handling. These smaller pieces of tissue are also suitable for the stretching procedure. Examples of such smaller pieces are rectangles with a longer dimension of about 5-8 cm.

Implantable biocompatible materials, such as for use in a prosthetic valve, can be selected based on, among other factors, compatibility with a subject in which the material will be implanted, physical properties of the material, such as thickness and consistency (e.g., the amount of variability in thickness over the surface area of a sample), and mechanical properties (e.g., elasticity or rigidity). In at least some cases, such as when biological tissue is used, mechanical properties of the implantable biocompatible material can be affected by the relative amounts of collagen and elastin.

Implantable biocompatible materials can be formed from a single material or from multiple materials, such as a multi-layer laminate. Laminate materials can be formed from sheets of the same implantable biocompatible material or from sheets of different implantable biocompatible materials, including mixtures of biological materials and synthetic materials. When the implantable biocompatible material is a multi-layer material, the constituent layers can be stretched before the composite is formed, or the composite can be stretched after assembly. In a particular example, one or more layers, such as a plurality of layers, are stretched before incorporation into the composite. For instance, two or more layers of the composite may be stretched separately before being incorporated into the composite.

Implantable biocompatible materials can be selected such that an implantable device into which a material is incorporated or formed has desired mechanical properties. For instance, different implantable biocompatible materials may have different degrees of viscoelasticity, and so may stretch to different degrees, including requiring different times to reach a point where viscoelastic creep has substantially ceased for a given set of conditions (e.g., at a given temperature and degree of tension). Stretching the layers prior to assembling the composite can result in improved properties in the composite, including implantable devices formed therefrom, such as having reduced propensity to creep during formation into a device and after implantation. Stretching the layers prior to forming the composite can also increase the stability of the composite, such as reducing any tendency of the composite to delaminate, particularly under applied stress.

Typically, the thickness of implantable biocompatible materials used to form an implantable device, such as a heart valve prosthesis, is also selected to provide desired physical and mechanical properties, such as having properties similar to native tissue in a subject (e.g., native heart valve leaflets). Larger heart valve leaflets (e.g., having a larger surface area) are typically thicker than smaller heart valve leaflets. Implantable biocompatible materials can be selected such that, after being pre-stretched according to a disclosed embodiment, the implantable biocompatible material has a desired final thickness. The desired thickness may be a thickness within a particular range (e.g., the implantable biocompatible material does not have a completely uniform thickness) and the implantable biocompatible material can have a desired degree of consistency in its thickness (e.g., the material does not vary more than a given percentage from an average, median, or desired thickness, or less than a particular amount of the material exceeds such a range).

In particular examples, implantable biocompatible material to be subjected to a disclosed pre-stretching process, including harvested tissue, has a thickness between about 100 microns and about 4000 microns, such as between about 200 microns and about 2000 microns, between about 200 microns and about 1000 microns, or between about 200 microns and about 900 microns. When the implantable biocompatible material is bovine pericardial tissue, harvested tissue typically has a thickness between about 250 microns and about 700 microns, more typically between about 300 microns and about 700 microns.

The final thickness of the implantable biocompatible material, including after being incorporated into an implantable device, is typically between about 50 microns and about 3000 microns, such as between about 100 microns and about 2000 microns, between about 150 microns and about 1000 microns, between about 160 microns and about 700 microns, between about 160 microns and about 650 microns, between about 150 microns and about 600 microns, between about 300 microns and about 600 microns, or between about 230 microns and about 580 microns. When the implantable biocompatible material is a composite material, the thickness of individual layers may be less than a range disclosed above, with the final composite having a thickness in an above-disclosed range.

As pre-stretching can reduce the thickness of the implantable biocompatible material, the material to be stretched can have a larger or greater thickness than the final desired thickness. For instance, if the implantable biocompatible material is expected to experience a thinning of 15% during a pre-stretching procedure, the starting thickness can be selected to be 115% of the desired final thickness. Similarly, other dimensions, such as the length or width, of the initial, unstretched implantable biocompatible material can be adjusted based on an expected degree of stretching or elongation, such as selecting a starting material that has a smaller length or width than a final dimension, where stretching produces a material having the final desired dimensions.

Implantable biocompatible materials, typically after pre-stretching, and optionally other preparative steps, can be cut to a desired shape to facilitate processing into an implantable device. In some cases, cutting can be carried out mechanically, such as using a suitably shaped die or a cutting tool. In other cases, non-mechanical techniques, such as laser cutting, can be used. In at least some cases, the starting implantable biocompatible material is dimensioned so that the final, stretched material has excess material. For example, having excess material can allow portions of the implantable biocompatible material coupled to a gripping member (in turn coupled to a tensioning member for applying a force to the gripping member and in turn the implantable biocompatible material) to be resected before being formed into an implantable device, or other processing steps.

Implantable biocompatible materials can be pretreated in manners other than stretching prior to implantation. Such pretreatments can be applied before or after incorporation of the implantable biocompatible material into an implantable device, and before or after pre-stretching. In particular implementations, such pretreatments are applied after pre-stretching, but before incorporating the implantable biocompatible material into an implantable device.

Pretreatment steps can include steps to stabilize the implantable biocompatible material, such as to prevent chemical changes to the material before or after the material is implanted. For instance, at least some implantable biocompatible materials can undergo calcification after implantation, which can result in stiffening or degradation of the material, which can affect the performance of an implantable device that uses the material, and potentially can lead to device failure. Accordingly, at least certain implantable biocompatible materials can be treating with a "capping" agent, where a capping agent blocks, removes, or alters a functional group of an implantable biocompatible material. Particular capping agents can be selected to help reduce calcification of the implantable biocompatible material. Suitable capping agents and techniques are disclosed in U.S. Pat. No. 9,351,829.

For at least some implantable biocompatible materials, such as tissue-based materials, pretreatment steps can include fixation, where cells and tissue components are preserved, such as from decay or alteration. Fixation is typically carried out by treating the implantable biocompatible material with a chemical agent, such as a chemical agent that crosslinks polypeptide chains within the same or adjacent collagen molecules. Examples of chemical fixative agents include dialdehyde starch, diamines, formaldehyde, glutaraldehyde, hexamethylene diisocyanate, and polyepoxy compounds. In a specific example, an implantable biocompatible material is fixed using a glutaraldehyde solution of between about 0.2 wt % and about 50 wt % glutaraldehyde, such as a solution having between about 0.2 wt % and about 8% wt % glutaraldehyde, between about 0.2 wt % and about 1.25 wt % glutaraldehyde, or between about 0.2 wt % and about 0.7 wt % glutaraldehyde.

After pre-stretching and any other pretreatment steps, an implantable biocompatible material may be stored prior to incorporation into an implantable device. The implantable biocompatible material may be stored in a liquid, such as in a solution (such as saline solution) having a low (e.g., 0.6 wt %) glutaraldehyde concentration. Alternatively, implantable biocompatible materials may be stored in a dry state, and rehydrated prior to incorporation into an implantable device. In a particular example, the implantable biocompatible material can be dehydrated in a mixture of glycerol and ethanol.

Implantable biocompatible materials can be sterilized, such as after stretching and any other pretreatment steps, including one or both of sterilizing the material prior to dehydration and after rehydration. Suitable sterilization methods include treating the implantable biocompatible material with ethylene oxide, gamma rays, or electron beam radiation. Glutaraldehyde can be used as a sterilization agent, as well as a fixative agent.

Figure 2:
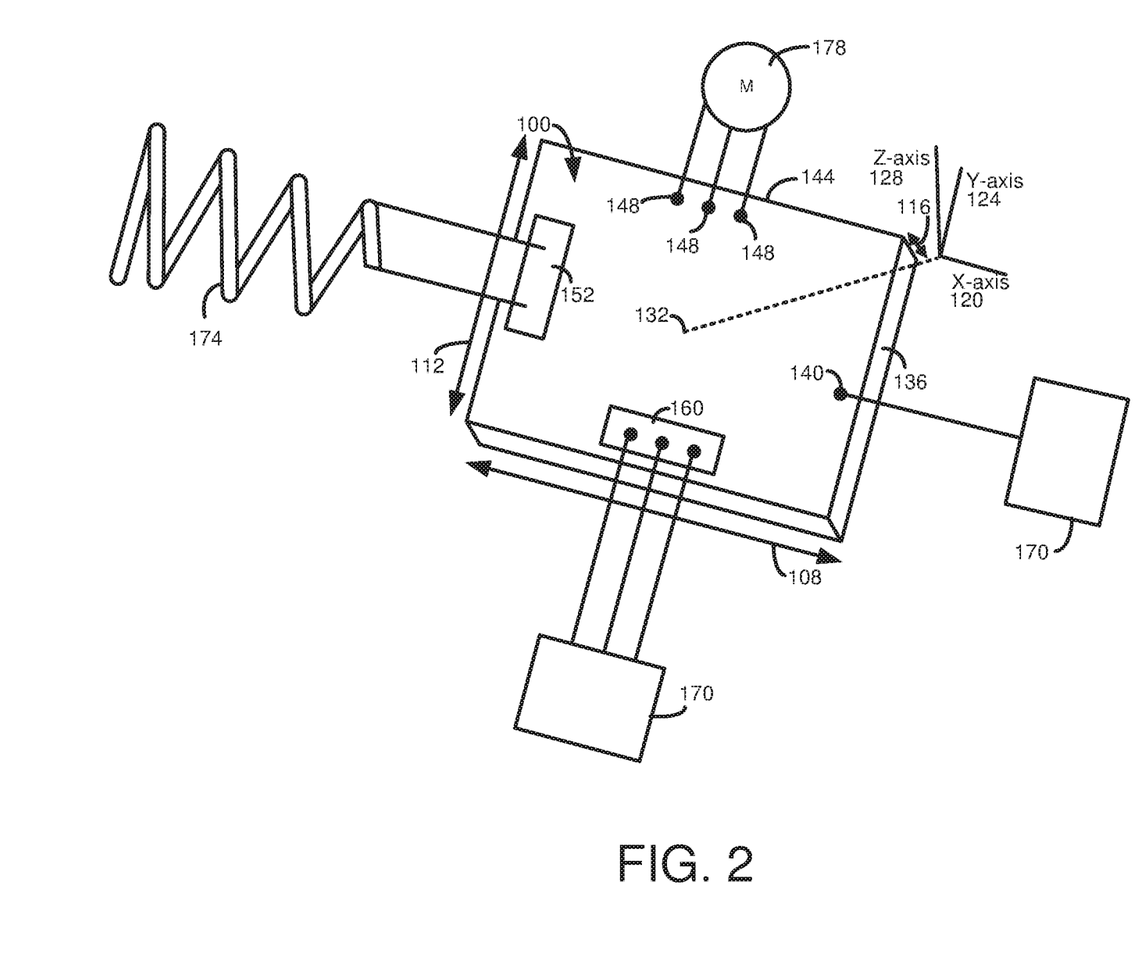
FIG. 2 illustrates a schematic diagram of an implantable biocompatible material, including various manners of applying tensioning forces to the material.

Pre-stretching can be applied to an implantable biocompatible material in one or more directions. With reference to FIG. 2, an implantable biocompatible material 100 can have a length 108, a width 112, and a thickness 116. A section or segment of implantable biocompatible material 100 can be generally referred to as a sheet. A sheet of material can have different shapes and dimensions, but typically has substantially larger length and width (or diameter) compared with the thickness of the material.

The implantable biocompatible material 100 is shown with reference to an X-axis 120 (generally corresponding to the length 108), a Y-axis 124 (generally corresponding to the width 112), and a Z-axis 128 (generally corresponding to the thickness 116), with an origin 132 located at the center of the implantable biocompatible material. A pulling or stretching force can be applied in a positive direction along the X-axis 120 (e.g., the material is pulled in the positive X-direction), in a negative direction along the X-axis, in a positive direction along the Y-axis 124, in a negative direction along the Y-axis, or a combination thereof.

In some examples, opposing tensioning forces are applied along an axis, such as an implantable biocompatible material being pulled in both positive and negative directions along the X-axis 120, along the Y-axis 124, or a combination thereof. In further examples, tensioning forces can be applied in perpendicular directions, such as pulling the implantable biocompatible material 100 in one or more directions (e.g., positive, negative) along a first axis and pulling the material in one or more directions along a second axis, where the first and second axes are perpendicular. When tensioning forces are applied in multiple directions, some or all of the directions may be non-opposing or non-perpendicular to another direction. For example, a tensioning force could be applied at an acute angle between pairs of perpendicular axes. Tensioning forces can also be applied radially outwardly relative to the origin 132, at a desired number of angles about the origin, including in the case of arcuate segments of implantable biocompatible material 100, or segments having a least one side that is not at least generally linear.

In some aspects, one or more directions in which an implantable biocompatible material is stretched can depend on the environment in which the material will be used, such as during or after incorporation into an implantable device, including after deployment of such an implantable device. For instance, it may be known that the implantable biocompatible material will experience tensioning forces along a first axis, but not in other directions (including a second axis perpendicular to the first axis). In some aspects, tension can be applied in directions where such forces will be applied to the implantable biocompatible material in use, but not in other directions, which can help maintain other native, desired properties of the implantable biocompatible material.

In other aspects, one or more directions in which an implantable biocompatible material is stretched can depend on the chemical, physical, or mechanical properties of the implantable biocompatible material. For instance, many biological materials, such as pericardial tissue, that may be incorporated into implantable devices contain significant amounts of structural proteins, such as collagen and elastin. These proteins can have particular orientations, such that the tissue may be more readily stretched in some directions than others. Accordingly, greater or lesser tensioning forces can be applied to an implantable biocompatible material depending on the viscoelastic properties (e.g., propensity to creep) of the material in particular directions and, if more uniform stretching is desired, the forces applied in different directions can be varied according to the degree of creep experienced in a particular direction. That is, for example, higher tension can be applied along an axis where stretching is more difficult than along an axis where stretching is easier.

Tensioning forces in a particular direction can be applied at a single point on the implantable biocompatible material or at multiple points. For example, if a section of implantable biocompatible material has a side (which can be fully or partially linear, or at least at a distinct angle from another side), the pulling force can be applied at multiple points along the side, which points can be symmetrically or unsymmetrically spaced. For instance, FIG. 1 illustrates a side 136 with a single attachment point 140 and a side 144 with multiple, evenly spaced attachment points 148.

An attachment point may contact all or a portion of a side of the implantable biocompatible material 100 when a single attachment point is used, or less than all of a portion of a side of the material when multiple attachments points are used. As shown in FIG. 1, attachment point 152 is a single attachment point, but has a larger surface area than the individual attachment points 148 or the single attachment point 140. Larger attachment points (e.g., having a larger surface area in contact with the implantable biocompatible material 100) may more evenly distribute a tensioning force, which can reduce any tendency of the implantable biocompatible material to become damaged during stretching, and may result in more even stretching, or otherwise impart more consistent properties to a particular portion of a material being stretched. Although the implantable biocompatible material 100 is shown as rectangular, the material can be of any desired shape, including arcuate shapes such as ellipses and circles (in which case attachment points can be located symmetrically or unsymmetrically along the perimeter of the material at points at which the material is to be stretched).

When multiple attachments points are used, tension may be applied symmetrically or unsymmetrically to the attachment points (and the symmetry may be different than the symmetry, or lack thereof, of the spacing of the multiple attachment points). For instance, if a pulling force provided by a 200 gram weight is to be applied to a side of the implantable biocompatible material 100, and there are four attachment points on the side, each attachment point could be coupled to a 50 gram weight, or some attachment points could be coupled to greater or lesser amounts of weight. Or, multiple attachment points could be attached to a single weight, such as having all four attachment points in the above example being attached to a single 200 gram weight (e.g., as shown for attachment point 160 of FIG. 1).

Applying unsymmetrical forces to a side of a section of implantable biocompatible material may be useful, for example, when different thicknesses or physical properties (including elasticity or propensity for further elongation when subjected to additional tension) are desired at different portions of the material. Applying unsymmetrical forces can also be useful when the material originally has different thicknesses at different locations. A weight distribution can be used to help increase the uniformity of the thickness (e.g., by applying larger forces to thicker locations, or otherwise applying larger forces to areas which are desired to be made thinner than other areas).

In some embodiments, a constant force is applied to the implantable biocompatible material during stretching, such as by tensioning the material with a constant amount of weight. Applying constant tension can help provide that the final properties of the implantable biocompatible material are suitable for an intended use. For instance, if an implantable biocompatible material is to be placed under a certain amount of tension after implantation (including resulting from its incorporation into an implantable device), it may be desirable to provide that the tension applied during stretching is greater than or equal to the tension experienced by the material after implantation. Applying an equal or greater amount of tension during a pre-stretching procedure can reduce (or eliminate) additional stretching (or creep) after implantation.

However, in some aspects, the tension applied to an implantable biocompatible material can be varied during a pre-stretching process. For instance, the pre-stretching process may be expedited by stretching the implantable biocompatible material using a higher tension for a period of time and then stretching the material using a lower tension, such as a tension closer to the tension the material will experience after-implantation, for a shorter period of time. Applying an initially higher tension and then a lower tension may, in at least some cases, produce equivalent results as stretching the material at lower, constant tension for a longer period of time. However, applying greater tension to the implantable biocompatible material may affect other properties of the material, even if an equivalent level of stretching is achieved as for applying a lower tension for a longer time. For instance, the rigidity (ability to resist bending, such as, with reference to FIG. 2, about the X-axis 120 or the Y-axis 124) of the implantable biocompatible material 100 may be reduced.

Tension may be applied to the implantable biocompatible material in any suitable manner. For instance, as mentioned above, a weight can be coupled to the implantable biocompatible material. In another example, a spring or other mechanical source of tension can be coupled to the implantable biocompatible material. When a spring is used, a spring can be selected having a suitable spring constant to provide the desired degree of tension. Tension may also be applied by an adjustable tensioning member, such as a threaded rod or cable tie (or another tensioning member having a ratcheting mechanism), coupled (directly or indirectly) to an implantable biocompatible material, where the tensioning member can be moved distally or proximally relative to the center of the material to increase or decrease the tensioning force. In other examples, tension is applied using a motor, for example, a stepper motor. Combinations of methods are also suitable.

As discussed above, in at least some cases, the tension applied to the implantable biocompatible material can be selected to achieve a desired degree of stretching, and may be related to the forces the material is expected to experience in vivo, including as a result of being incorporated into an implantable device. The amount of tension needed to produce a desired degree of stretching (or other preconditioning) can depend on the physical properties of the material, such as its viscoelasticity. Typically, more viscoelastic materials typically need lower tension to achieve a desired degree of stretching than less viscoelastic materials.

When applied as a weight, such as a dead weight (e.g., attached to one end of an implantable biocompatible material), the weight can be between about 300 grams (about 3 N) and about 4000 grams (about 40 N) for bovine pericardial tissue or a material having a viscoelasticity similar to bovine pericardial tissue (e.g., having a stress/strain curve or length/time curve that is at least about 80% similar to that of bovine pericardial tissue, such as being at least about 85%, at least about 90%, at least about 95%, at least about 99%, or about 100% similar to that of bovine pericardial tissue). In more particular examples, the weight can be between about 300 grams and about 3000 grams, between about 300 grams and about 2000 grams, between about 300 grams and about 1000 grams, between about 325 grams and about 800 grams, between about 350 grams and about 650 grams, between about 400 grams and about 1000 grams, between about 400 grams and about 800 grams, between about 400 grams and about 700 grams, between about 400 grams and about 600 grams, between about 450 grams and about 550 grams, or about 500 grams. Such tensile loads are suitable for the pieces of pericardial tissue of the dimensions discussed above.

The weight can be adjusted to account for implantable biocompatible materials having a different viscoelasticity than bovine pericardial tissue, such as by increasing or decreasing the weight proportionally to the difference in viscoelasticity between the materials. When tension is applied other than as a weight (e.g., by a tensioning member, such as a rod, a spring, or a motor), the force can be at least substantially equivalent to the force applied by a weight in an above-described range.

A tensioning member or mechanism, such as a weight (FIG. 2, 170), spring (174), or motor (178) can be applied to the implantable biocompatible material 100 in any suitable manner. For instance, a tensioning member can be coupled to, or include, one or more securing members, where a securing member secures the tensioning member to the implantable biocompatible material and transmits the tensioning force to the material. A securing member can be a component that pierces through all or a portion of the implantable biocompatible material, such barbs, hooks, pins, or sutures. As another example, the securing member can be a clamp (such as an alligator clamp) that compresses one or more surfaces of the implantable biocompatible material. In some cases, a securing mechanism can use suction to attach a tensioning member to the implantable biocompatible material, which can also apply all or a portion of the tension. The implantable biocompatible material may be coupled to a tensioning member using an adhesive as the securing member. The adhesive can be a biodegradable adhesive, such as fibrin, or a non-biodegradable adhesive, such as cyanoacrylate.

The implantable biocompatible material is typically maintained at an elevated temperature during stretching. More particularly, the implantable biocompatible material is typically maintained at a temperature that is at least substantially the same as a temperature of an environment into which the material will be implanted, such as a physiological temperature. In further aspects, the implantable biocompatible material can be stretched while being maintained at a temperature that is higher than a temperature of an environment into which the material will be implanted.

Maintaining the implantable biocompatible material at a temperature that is at least substantially the same as its implantation environment can help provide that the material undergoes at least as much stretching as it would in the implantation environment. Maintaining the implantable biocompatible material at a higher temperature than an implantation environment can result in a greater degree of stretching than would be experienced in the implantation environment. Thus, maintaining the implantable biocompatible material at a higher temperature can also help reduce, including in some cases eliminating, any further stretching after the material is implanted.

A temperature that is at least substantially the same as a temperature of an environment into which the implantable biocompatible material will be implanted can be a temperature that is at least about 85%, at least about 90%, at least about 95%, or at least about 99% of the temperature of the implantation environment. The temperature used during pre-stretching can be between such a temperature and a temperature at which the implantable biocompatible material experiences undesired physical, mechanical, or chemical changes, where the upper temperature in a range can vary for different materials. In some cases, the upper temperature in a range can be a temperature that is less than about 150%, less than about 145%, less than about 140%, less than about 135%, less than about 130%, less than about 125%, less than about 120%, less than about 115%, less than about 110%, or less than about 105% of the temperature (such as the average temperature) of an environment into which the implantable biocompatible material will be implanted. In more specific examples, the temperature can be a range between a lower temperature recited herein (e.g., an "at least about" temperature) and a higher temperature recited herein (e.g., a "less than about" temperature).

In various examples, the temperature at which the implantable biocompatible material is maintained during stretching can be between about 30° C. and about 46° C. or between about 30° C. and about 41° C., such as between about 32° C. and about 44° C., between about 35° C. and about 41° C., between about 36° C. and about 39° C., between about 37° C. and about 38° C., or about 37° C. As discussed above, typically, the implantable biocompatible material is maintained at a temperature that is less than a temperature at which the material would undergo undesired physical or chemical changes. Higher temperatures can allow for a larger degree of stretching in a shorter amount of time, and potentially lower tension to be used. For bovine pericardial tissue, the temperature at which undesired changes can occur to the tissue can be between about 80° C. and about 95° C. depending on any pretreatments that may have been applied (e.g., treatment with a fixative, such as glutaraldehyde). Thus, in further examples, the implantable biocompatible material, and in particular bovine pericardial tissue, can be maintained at a temperature within a range between an above listed temperature (including a temperature in an above listed range) and about 80° C., about 85° C., about 90° C., or about 95° C.

During stretching, the implantable biocompatible material can be heated, or maintained, at a temperature including, in a least some cases, by maintaining the material in a liquid (such as in a bath) having the desired temperature. When maintained in a liquid, such as a saline solution, the solution can include other components to help condition or stabilize the implantable biocompatible material, or to modify various properties of the material. However, heat can be applied in any suitable manner, including using other fluids, such as gaseous fluids, to transfer heat to the implantable biocompatible material. Or, the implantable biocompatible material can be contacted with a solid object that is heated to the desired temperature, or otherwise supplies heat to the material.

Tensioning of the implantable biocompatible material can be carried out for a time sufficient to produce a desired amount of elongation. In particular cases, tensioning is carried out for a period of time until the rate of elongation experiences a substantial decrease (such as a consistent decrease, such as a decrease that persists for at least about 15 minutes, at least about 30 minutes, at least about 1 hour, or at least about 2 hours). In various examples, the implantable biocompatible material is stretched until the rate of elongation is less than about 70% of the initial stretching rate (such as, for example, the average stretching rate over a period of time, such as a period of time within the first six hours of stretching, such as the first five hours, four hours, three hours, two hours, hour, half hour, or fifteen minutes of stretching). More particularly, tensioning can be carried out until the rate of elongation is less than about 25%, about 20%, about 15%, about 10%, about 5%, about 2%, about 1%, or less than about 1% of such an average initial elongation rate. In specific examples, tensioning, such as tensioning using a tension in an above-described range, is carried out for at least about 1 day, such as at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, or at least about 21 days, such as between about 1 day and about 45 days, between about 1 day and about 21 days, between about 7 days and about 21 days, between about 10 days and about 21 days, between about 11 days and about 45 days, between about 11 days and about 30 days, between about 11 days and about 21 days, between about 12 days and about 21 days, between about 13 days and about 21 days, between about 14 days and about 45 days, between about 14 days and about 21 days, or between about 14 days and about 18 days.

In at least some embodiments, the implantable biocompatible material is stretched without a compressive force being applied, such as a compressive force directed orthogonally to a stretching direction, or a generally flat or planar surface of the material (e.g., compressing the thickness of the material). This lack of compression can allow the final, stretched implantable biocompatible material to retain a compression ratio that is at least substantially similar to the original unstretched material, allowing the material to be further compressed, such as when the material is, or is being, incorporated into an implantable device.

After an implantable biocompatible material has been stretched to a desired degree, it can be incorporated into an implantable device. Example methods of forming implantable devices, including prosthetic heart valves, from implantable biocompatible materials are disclosed in U.S. Patent Publication No. 2003/0027332. The implantable biocompatible material can be cut to a desired shape and size, including using a technique described above. The implantable biocompatible material can be subjected to additional pretreatments (that is, a post-treatment with respect to a pre-stretching procedure, but being a pre-treatment with respect to incorporation of the pre-stretched material into an implantable device), including pretreatments steps described above, such as capping, fixation, or sterilization. The implantable biocompatible material may also be stored prior to use, including in a hydrated or dehydrated state.

In a specific implementation, un-fixed or partially fixed implantable biological materials are subjected to a disclosed pre-stretching procedure and are fixed after being stretched to a desired degree. Fixing conditions described above for "pre-treatments" can be used for post-stretching fixation. It may be beneficial to use higher glutaraldehyde concentrations for post-stretching fixation, such as using a solution having between about 1.25 wt % and about 50% glutaraldehyde or between about 1.25 wt % and about 8 wt % glutaraldehyde.

Using partially fixed or unfixed tissue for a thinning or stretching procedure can be beneficial, as unfixed or partially fixed material may stretch more quickly, to a larger extent, with lesser force, or a combination of these features compared with partially- or fully-fixed material. That is, fixing the implantable biocompatible material prior to stretching may reduce the ability of the material to stretch, thus potentially requiring longer stretching times or higher degrees of tension to achieve an equivalent degree of stretching or thinning as compared with unfixed material. Additionally, fixed or partially fixed implantable biocompatible material may not be capable of the same maximum stretching or thinning as unfixed or less fixed material. Further, waiting to fix, or fully fix, the implantable biocompatible material until after a desired degree of stretching has been performed can help "lock in" the stretch. Similar considerations can apply to the timing of other material treatments, such as sterilization of the implantable biocompatible material, including the use of terminal liquid sterilization procedures (e.g., heating the material in a closed container immersed in a liquid sterilant).

As used herein, "partially fixed" can refer to a level of fixation, such as a level of crosslinking in an implantable biocompatible material, that is between that of an unfixed material and that of a "fully-fixed" material, where a fully fixed material can be determined with respect to a final fixation level that is to be achieved (e.g., "fully fixed" with respect to a final fixation level for a particular material in a particular process), or with respect to conditions that are generally understood to provide fixed materials. In particular examples, "partially-fixed" can be defined with respect to a level of crosslinking, such as the level being between about 15% and about 85% of the level present in fully-fixed implantable biocompatible materials, such as being between about 25% and about 80%, between about 35% and about 75%, between about 40% and about 65%, or between about 45% and about 60% of the level of crosslinking in a fully-fixed implantable biocompatible material.

In a specific implementation, non-fixed implantable biocompatible material, implantable biocompatible material that has been fully or partially fixed, but not sterilized, or implantable biocompatible material that has been sterilized and/or fully or partially fixed, but maintained in a non-fixating solution (e.g., water, saline, other non-fixating solutions, or combinations thereof) for a prolonged duration (e.g., at least one hour, at least 12 hours, at least 1 day, at least 3 days, at least 7 days, at least 28 days, optionally with an upper bound of exposure, such as at most 3 months, at most 6 months, or at most 1 year) is subjected to a stretching process, and the pre-stretched material is then treated with a fixative agent, such as glutaraldehyde, and then optionally sterilized, such as using terminal liquid sterilization. In another implementation, non-fixed implantable biocompatible material, implantable biocompatible material that has been fully or partially fixed, but not sterilized, or implantable biocompatible material that has been sterilized and/or fully or partially fixed, but maintained in a non-fixating solution (as described above) for a prolonged duration (as described above) is subjected to a stretching process, and the pre-stretched material is then treated with a fixative agent, such as glutaraldehyde, while the material is being maintained under tension. In a particular example, the implantable biocompatible material is sterilized after the fixed, stretched material has been released from tension. In another example, the implantable biocompatible material is both fixed and sterilized while under tension. In some cases, applying a serialization procedure, such as one involving heat treatment, while an implantable biocompatible material is under tension can induce additional stretching/thinning in the material.

When the implantable biocompatible material is stored, or during manipulation or fabrication steps, the material can be maintained in a suitable solution, such as a solution having an appropriate pH. In particular examples, the solution can have a pH of between about 6 and about 10, such as between about 6.9 and 9. Solutions may be buffered at a particular pH or within a particular pH range, including using buffering agents such as ammonium, bicarbonate, borate, cacodylate, carbonate, and organic buffers such as morpholine propanesulfonic acid, N-(2-hydroxyethyl)piperazine-N'-(2-ethanesulfonic acid) (HEPES), or tris(hydroxymethyl)aminomethane (TRIS).

The present disclosure lists values and ranges for various pre-stretching parameters, including applied tension, stretching time (or an elongation rate at which tension is released), and temperature. It should be understood that the present disclosure embraces any value or range of one parameter being used in combination with any recited value or range for any other parameters. However, in particular examples, the applied tension is between about between about 400 grams and 1000 grams (or an intermediate range), the temperature is maintained at a temperature of between about 35° C. and about 41° C. (or an intermediate range), and the tension is applied for a period of between about 11 days and about 45 days (or an intermediate range).

EXAMPLE

Eight samples of bovine pericardium tissue were obtained. A constant force (dead weight of 500 grams) was applied to the samples for a period of two weeks. During this stretching, the samples were maintained in a warm bath (37° C.).

Figure 3:
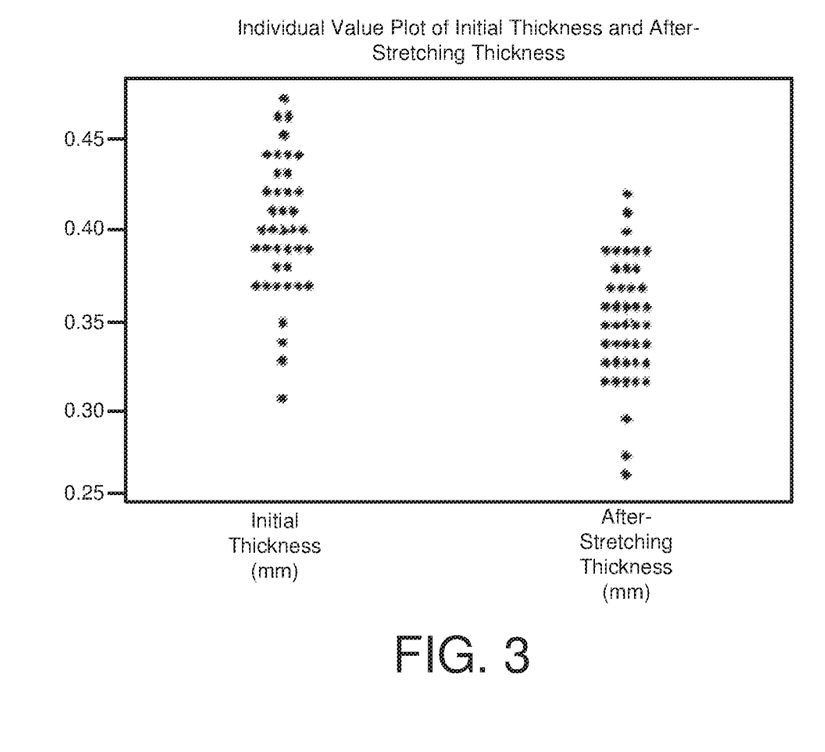
FIG. 3 is a graph of measured thickness values (mm) for bovine pericardial tissue samples before (initial) and after (creep) applying tensioning forces to the tissue for a period of two weeks.

The thickness of the samples was measured before and after the stretching. FIG. 3 is a plot of individual thickness values (mm) for the samples at their initial thickness and at their thickness after being stretched.

Figure 4:
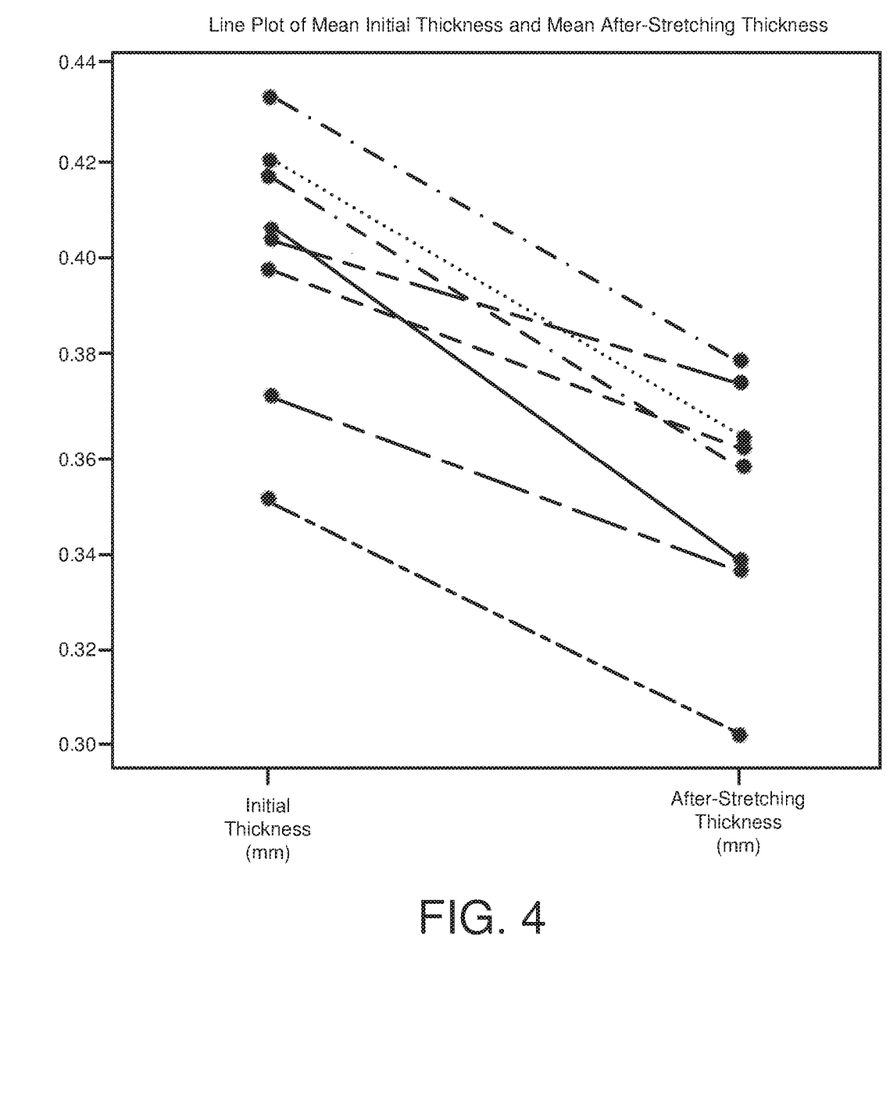
FIG. 4 is a plot of measured thickness values (mm) for individual bovine pericardial tissue samples before and after applying tensioning forces to the tissue for a period of two weeks.

FIG. 4 is plot of initial thickness and final thickness of the eight samples. Although the samples varied in their initial thickness, each of the samples underwent significant thinning during the stretching process, as evidenced by the final thickness values. The samples stretched an average of about 12.5%, or 0.05 mm.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth above. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

Unless otherwise indicated, all numbers expressing quantities of components, percentages, temperatures, times, and so forth, as used in the specification or claims that are modified by the term "about" should also be understood to include the recited values and ranges as exact numbers, not modified by "about." Unless otherwise indicated, implicitly or explicitly, the numerical parameters set forth as approximations may depend on the desired properties sought and/or limits of detection under standard test conditions/methods.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A method of pre-stretching an implantable biocompatible material comprising:
applying a tensioning force of between about 300 grams and about 4000 grams to the sheet of implantable biocompatible material;
while applying the tensioning force, maintaining the sheet of implantable biocompatible material at a temperature that is at least substantially as high as a temperature of an environment into which at least a portion of the implantable biocompatible material will be implanted;
maintaining the sheet of implantable biocompatible material under tension until the sheet experiences a substantial decrease in an elongation rate of the sheet, providing a pre-stretched implantable biocompatible material;
forming one or more prosthetic heart valve leaflets from the pre-stretched implantable biocompatible material; and
incorporating the one or more prosthetic heart valve leaflets into a prosthetic heart valve.

2. The method of claim 1, wherein the temperature is between about 30° C. and about 95° C.

3. The method of claim 1, wherein the tensioning force is between about 300 grams and about 1000 grams.

4. The method of claim 1, wherein the tensioning force is applied for a period of between about 1 day and about 45 days.

5. The method of claim 1, wherein the implantable biocompatible material comprises pericardial tissue.

6. The method of claim 1, wherein the sheet of implantable biocompatible material is maintained under tension until the elongation rate is less than about 25% of an average initial elongation rate.

7. The method of claim 1, wherein the sheet of implantable biocompatible material is maintained under tension until the elongation rate is less than about 10% of an average initial elongation rate.

8. The method of claim 1, wherein the tensioning force is applied along a single axis.

9. The method of claim 1, wherein the tensioning force is applied along multiple axes.

10. The method of claim 1, further comprising implanting the prosthetic heart valve in a subject.

11. The method of claim 1, wherein the implantable biocompatible material is unfixed when the tensioning force is applied and the implantable biocompatible material is fixed while under tension.

12. The method of claim 11, wherein the implantable biocompatible material is unsterilized when the tensioning force is applied.

13. The method of claim 12, wherein the implantable biocompatible material is sterilized while under tension.

14. The method of claim 1, wherein the implantable biocompatible material is partially fixed when the tensioning force is applied and the implantable biocompatible material is fixed while under tension.

15. The method of claim 1, wherein the implantable biocompatible material is an at least partially fixed implantable biocompatible material maintained in a non-fixative solution for at least about one hour prior to applying tension to the implantable biocompatible material.

16. A method of pre-stretching pericardial tissue comprising:
    applying a tensioning force of between about 400 grams and about 1000 grams to the sheet of pericardial tissue;
    while applying the tensioning force, maintaining the sheet of pericardial tissue at a temperature of between about 30° C. and about 46° C.;
    maintaining the sheet of pericardial tissue under tension until the elongation rate of the sheet is less than about 10% of an average initial elongation rate to provide a pre-stretched implantable biocompatible material, where the average initial elongation rate is the elongation rate over the first hour in which tension is applied;
    forming one or more prosthetic heart valve leaflets from the pre-stretched implantable biocompatible material; and
    incorporating the pre-stretched implantable biocompatible material into a prosthetic heart valve.

17. A method of forming a prosthetic valve, comprising:
    applying a tensioning force of between about 400 grams and about 1000 grams to the sheet of pericardial tissue;
    while applying the tensioning force, maintaining the sheet of pericardial tissue at a temperature of between about 30° C. and about 46° C.;
    maintaining the sheet of pericardial tissue under tension until the elongation rate of the sheet is less than about 10% of an average initial elongation rate, where the average initial elongation rate is the elongation rate over the first hour in which tension is applied; and
    attaching at least a portion of the sheet of elongated pericardial tissue to a frame of a prosthetic heart valve.

\* \* \* \* \*